(12) United States Patent
Martin (10) Patent No.: US 9,758,755 B2
(45) Date of Patent: Sep. 12, 2017

(54) FILTER-BASED METHOD FOR EFFICIENT CAPTURE OF LYSIS OF SUSPENDED CELLS

(71) Applicant: LIFE TECHNOLOGIES CORPORATION, Carlsbad, CA (US)

(72) Inventor: Philip Martin, Carlsbad, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 14/921,741

(22) Filed: Oct. 23, 2015

(65) Prior Publication Data
US 2017/0114317 A1   Apr. 27, 2017

(51) Int. Cl.
| | | |
|---|---|---|
| *C12N 1/06* | (2006.01) | |
| *C12M 1/00* | (2006.01) | |
| *C07K 1/22* | (2006.01) | |
| *C07K 1/18* | (2006.01) | |
| *C07K 1/16* | (2006.01) | |

(52) U.S. Cl.
CPC ............ *C12M 47/06* (2013.01); *C07K 1/16* (2013.01); *C07K 1/18* (2013.01); *C07K 1/22* (2013.01); *C12M 29/04* (2013.01); *C12M 29/16* (2013.01)

(58) Field of Classification Search
None
See application file for complete search history.

(56) References Cited

U.S. PATENT DOCUMENTS

| | | | | | |
|---|---|---|---|---|---|
| 5,187,083 | A * | 2/1993 | Mullis | ...................... | C12N 1/06 435/259 |
| 6,136,555 | A * | 10/2000 | Jones | ................... | B01J 19/0046 210/321.6 |
| 2003/0170810 | A1* | 9/2003 | Vedadi | ................. | B01D 15/361 435/69.1 |
| 2009/0166290 | A1* | 7/2009 | Andersson | ........... | B01D 61/145 210/636 |
| 2009/0325269 | A1 | 12/2009 | Marschke | | |
| 2013/0337528 | A1* | 12/2013 | Thompson | ........... | B01D 69/144 435/178 |
| 2014/0295503 | A1* | 10/2014 | Protozanova | ...... | C12N 15/1013 435/91.53 |
| 2014/0356890 | A1 | 12/2014 | Lee et al. | | |
| 2016/0304828 | A1* | 10/2016 | Stanton | .................. | C12M 45/02 |

FOREIGN PATENT DOCUMENTS

| | | |
|---|---|---|
| EP | 2602315 | 6/2013 |
| WO | 0110886 | 2/2001 |
| WO | 0177316 | 10/2001 |
| WO | 0206456 | 1/2002 |
| WO | 2014151177 | 9/2014 |

OTHER PUBLICATIONS

Dai, X. et al. An Integrated Membrane Based Chromatographic Process for Biomolecule Isolation and Purification. Dissertation Abstracts International 61(5B) 183 pages, Order No. AAI9971408.*
Kesberg, A. et al., "Improved protocol for recovery of bacterial DNA from water filters: Sonication and backflushing of commercial syringe filters", *Journal of Microbiological Methods*, vol. 93, No. 1, Feb. 16, 2013, 55-57.
Mueller, J. et al., "Variables Influencing Extraction of Nucleic Acids from Microbial Plankton (Viruses, Bacteria, and Protists) Collected on Nanoporous Aluminum Oxide Filters", *Applied and Environmental Microbiology*, vol. 80, No. 13, Apr. 18, 2014, 3930-3942.
O'Mahony, K. et al., "Proposal for a better integration of bacterial lysis into the production of plasmid DNA at large scale", *Journal of Biotechnology*, vol. 119, No. 2, Sep. 23, 2005, 118-132.
Steward, G. et al., "Extraction and purification of nucleic acids from viruses", *Manual of Aquatic Viral Ecology*, 2010, American Society of Limnology and Oceanography, 154-165.

* cited by examiner

*Primary Examiner* — Ralph Gitomer (57) ABSTRACT

A cell lysis workflow involving a cell suspension that is passed through a filter in a first flow direction from a first side of the filter toward a second side thereof. The filter captures a plurality of cells on the first side. A lysis solution is passed through the filter in a second flow direction opposite the first direction, thereby dislodging the plurality of cells captured on the filter, and resuspending the plurality of cells in the lysis solution on the first side of the filter. The lysis solution lyses the plurality of cells to produce a cellular lysate. The cellular lysate is passed through the filter in the first flow direction.

14 Claims, 7 Drawing Sheets

FILTER-BASED METHOD FOR EFFICIENT CAPTURE OF LYSIS OF SUSPENDED CELLS

TECHNICAL FIELD

This application relates to methods for extracting protein from cells suspended in a liquid cell culture medium, and, more particularly, to automated systems and methods for cell capture, lysis, and protein clarification from liquid cell cultures.

BACKGROUND

Many existing methods for protein extraction and purification from liquid cell cultures are time-intensive, largely manual processes. These methods requiring technical expertise and specialized equipment to perform various steps of the methods. For example, one typical procedure would include centrifugation of the liquid cell culture to harvest the cells, followed by resuspension of the resultant cell pellet in a lysis buffer to lyse the cells. The lysate is then clarified through an additional centrifugation step, where the clarified lysate is decanted for collection. The clarified lysate may then be run through a protein purification column to further purify the desired protein for collection in an elution buffer for further downstream workflows.

SUMMARY

In one aspect, a cell lysis workflow is disclosed. A cell suspension is passed through a filter in a first flow direction from a first side of the filter toward a second side thereof. The filter captures a plurality of cells on the first side. A lysis solution is passed through the filter in a second flow direction opposite the first direction, thereby dislodging the plurality of cells captured on the filter, and resuspending the plurality of cells in the lysis solution on the first side of the filter. The lysis solution lyses the plurality of cells to produce a cellular lysate. The cellular lysate is passed through the filter in the first flow direction.

In another aspect, a cell lysis system is disclosed. The system includes a filter sized to allow fluid to pass therethrough and to filter out cells, a reservoir in fluid communication with the filter and positioned on a first side thereof, a cell suspension intake in fluid communication with the filter and positioned on the first side thereof, a lysis solution intake in fluid communication with the filter and positioned on a second side thereof, and a reversible pump in fluid communication with the filter. The reversible pump has a first operating state to facilitate fluid flow in a first flow direction through the filter from the first side toward the second side thereof, and a second operating state to facilitate fluid flow in a second flow direction through the filter from the second side toward the first side thereof. The cell suspension intake is configured to receive a cell suspension therethrough such that the cell suspension is filtered through the filter and a plurality of cells of the cell suspension are captured on the first side of the filter when the reversible pump is in the first operating state. The lysis solution intake is configured to receive a lysis solution therethrough such that the lysis solution passes through the filter in the second flow direction when the reversible pump is in the second operating state to lyse and suspend the plurality of cells captured on the first side of the filter to produce a cellular lysate. The reservoir is configured to receive the cellular lysate when the reversible pump is in the second operating state.

Other aspects of the disclosed cell lysis workflow and system will become apparent from the following description, the accompanying drawings, and the appended claims.

DETAILED DESCRIPTION

Figure 1:
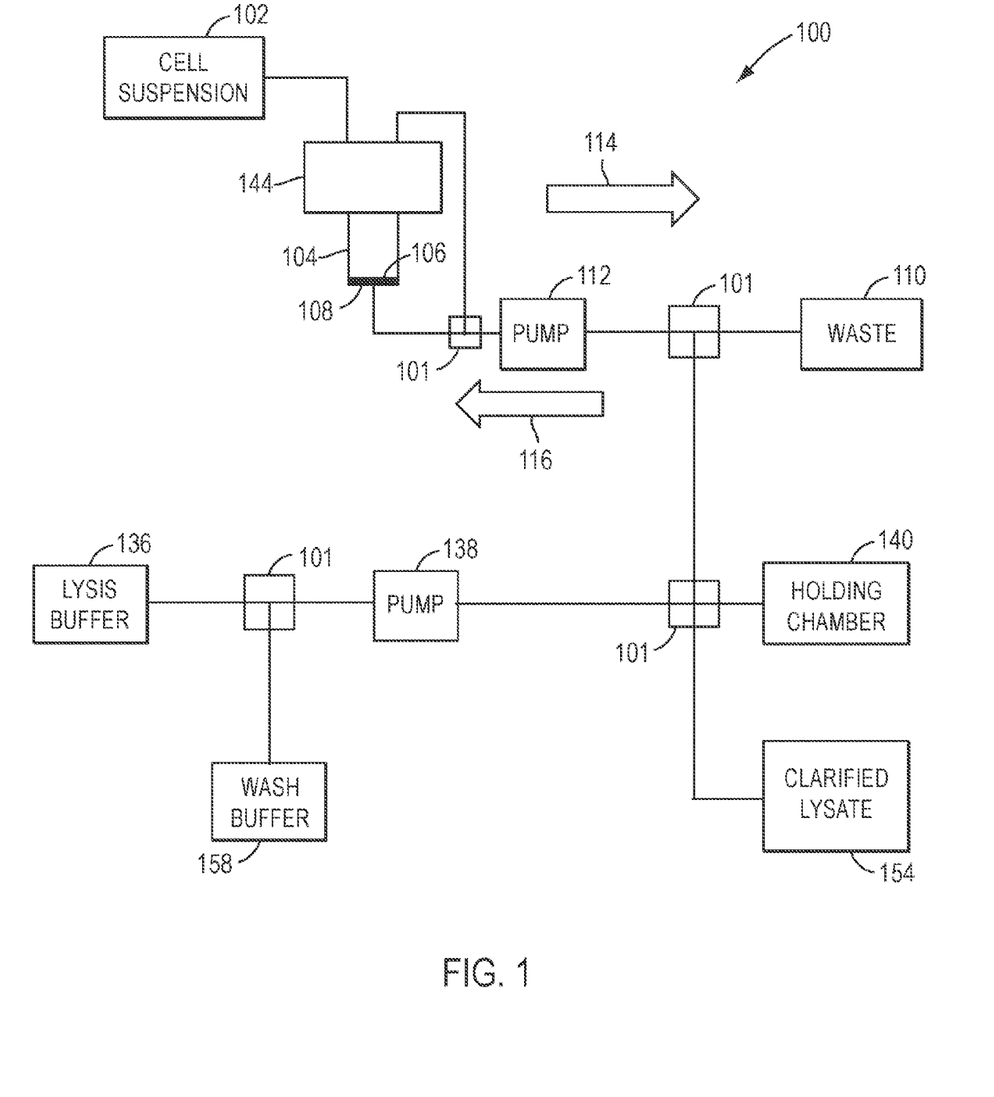
FIG. 1 schematically depicts one embodiment of a cell lysis workflow.

Referring now to FIG. 1, an embodiment of a cell lysis system or workflow, generally designated 100, is shown. It should be appreciated that in operation, the alternative pathways represented in the schematic diagram by various junctions 101 may include manual or automatic valves or the like to control and direct the flow of fluid, or alternately, distinct fluid lines may be included to facilitate some or all of the different pathways.

A cell suspension 102 is provided and may include any of a variety of eukaryotic and/or prokaryotic cells. In one embodiment, the cells are mammalian cells, or more particularly, rodent (e.g., mouse, rat, or hamster) such as CHO cells, or primate/human cells such as 293 or COS cells. In another embodiment, the cells are prokaryotic, for example bacterial cells such as *E. coli*. The cells may contain an expressed protein desired to be purified and collected.

Cells from the suspension 102 are passed through a filter 104 and captured by filtration on a first side 106 of the filter 104. The filtrate 126 (FIG. 3A and FIG. 3B) passes through the filter 104 and past a second side 108 thereof, and may be directed toward a waste receptacle 110. Completion of this and each subsequent step may optionally be detected by an air/bubble sensor (not shown), or by any other methods for detecting the cessation of fluid flow or sufficiently low flow rates known to the skilled practitioner, and in the case of an automated workflow, a controller is then directed to perform the subsequent step. A reversible pump 112, which in one embodiment may be a peristaltic pump, is positioned to create negative pressure on the filter 104/suspension 102 and cause the cells and media to be drawn in and through the filter 104 in a first flow direction, generally designated by arrow 114, when the pump 112 is in a first operating state. The reversible pump 112 also has a second operating state to generate positive pressure on the filter 104, which facilitates liquid flow in an opposite, second flow direction, generally designated by arrow 116.

Figures 3A, 3B:
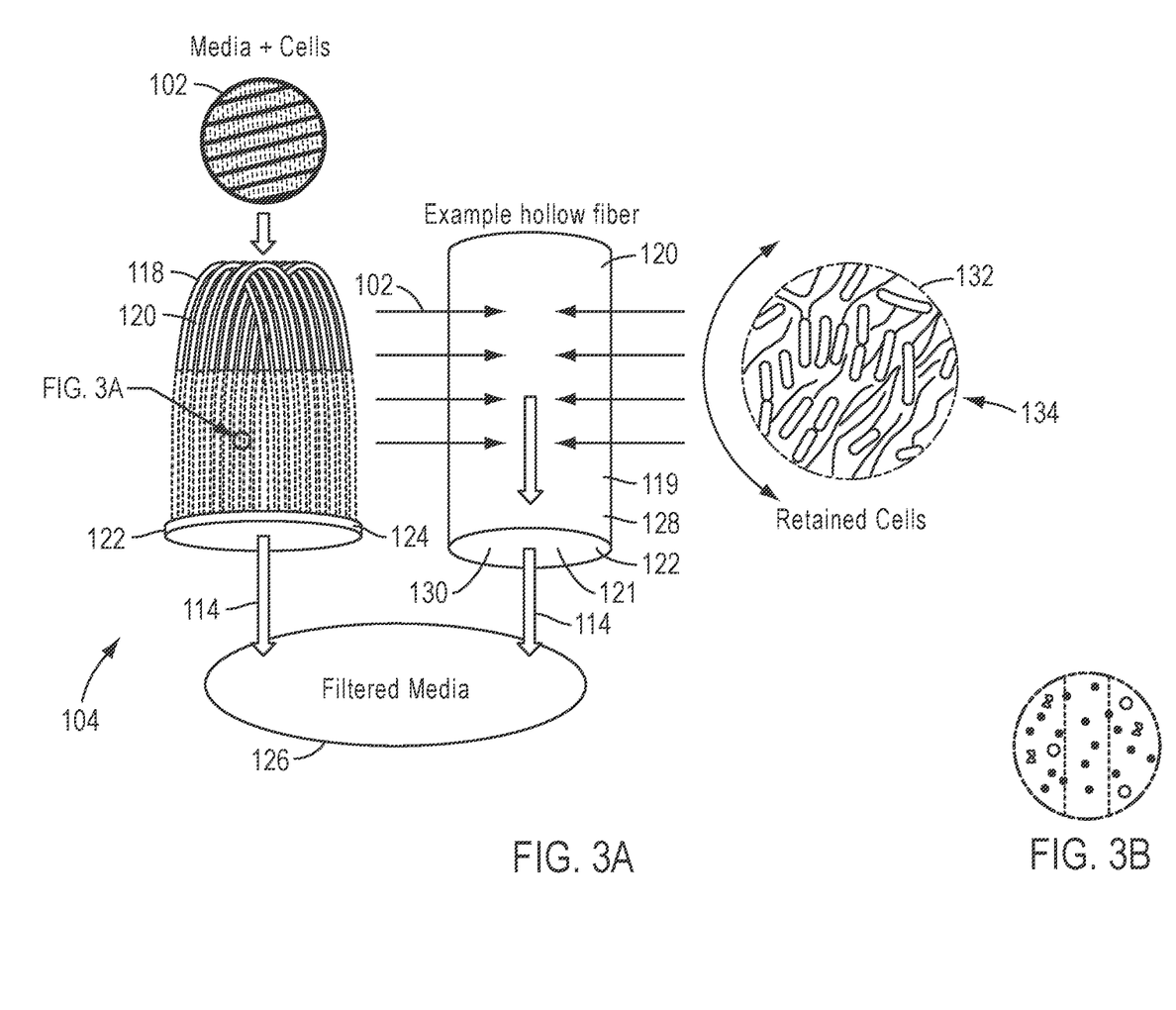
FIG. 3A and FIG. 3B depicts an embodiment of a filter suitable for use with the workflows of FIG. 1 and FIG. 2.

In certain embodiments, a suitable filter system 104 is selected primarily based on its flow rate and filter capacity. Additionally, a suitable filter system 104 should have an adequate pore size to capture the cells to be lysed. In one embodiment in which *E. coli* are captured on a membrane system and subsequently subjected to lysis, a 0.2 µm hollow fiber filter membrane may be used. Referring additionally to FIG. 3A and FIG. 3B, in one embodiment, the filter 104 includes a plurality of cellulose acetate-based porous hollow fibers 120, bent into a series of loops 118. This collection of loops 118 gives the filter 104 a large surface area. The open ends 122 of these loops 118 are potted into polyurethane or some similar polymer to form an end plug 124 (machined to ensure that the open ends 122 of the loops 118 remain open). In one embodiment, the hollow fiber filter 104 may be a MEDIAKAP® filter commercially available from SPECTRUM® Laboratories, Inc., such as the MEDIAKAP-25 filter.

Still referring to FIGS. 1 and 3A and 3B, filtration of the suspension 102 is achieved by adding the cell suspension 102 to the outside of the hollow fiber filter 104 and subjecting the suspension to a vacuum applied across the filter 104 in the first flow direction 114. This action draws liquid and sufficiently-small particles of the cell suspension 102 through the wall 128 of the hollow fibers 120 of the filter 104 and down internal lumens 130 within the hollow fibers 120. The cells 132 of the cell suspension 102 are captured in filter fibers 134 that form the external surface of the wall 128. The filtrate 126 then passes out of the lumen 130 and beyond the polymer plug 124. Accordingly, in this embodiment of the filter 104, the outside 119 of the wall 128 (FIG. 3A and FIG. 3B) defines the first side 106 of the filter 104 (FIG. 1), and the inside 121 of the wall 128 (bounding the internal lumen 130) (FIG. 3A and FIG. 3B) defines the second side 108 of the filter 104 (FIG. 1). It will be readily appreciated that any number of other filter configurations (including alternative hollow fiber filter configurations and various selective membrane-based filter systems) may be employed to capture the cells 132 on the first side 106 of the filter 104 and permit passage of the filtrate 126 through to the second side 108 the filter 104.

After the cell suspension 102 is filtered through the filter 104, a lysis buffer or solution 136 (FIG. 1) is added to the cells 132 captured on the filter 104 to lyse the cells 132. A requisite amount of a lysis buffer 136 suitable for lysing the captured cells 132 on the first side 106 of the filter 104 is dispensed manually and/or by an automated pump system 138. In one embodiment, the pump system 138 is a syringe pump with two way valving to direct flow and provide precise control of the dispensed volume of lysis buffer 136. One or more optional holding chambers 140 may be positioned between the pump system 138 and the reversible pump 112 to temporarily retain dispensed lysis buffer 136 (and/or other buffers, wash solutions, and the like for use in the workflow 100) before the lysis buffer 136 is added to the cells 132, such that the pump system 138 controls flow of the lysis buffer 136 to the holding chamber 140, but the reversible pump controls flow of the lysis buffer 136 to the filter 104.

As discussed in more detail below, the lysis buffer 136 may be supplied to the first side 106 of the filter 104 in any of a variety of ways to lyse the cells 132 captured on the filter 104, which releases their contents, to produce a lysate including the target protein or other target material. Once added, the lysis buffer 136 may be retained on the first side 106 of the filter 104 for an optional incubation period, which, in one embodiment, may be about 1-30 minutes. After the incubation period is complete, the reversible pump 112 is operated to pump the lysate 136 in the first flow direction 114 to filter the lysate through the filter 104 to produce a clarified lysate 154 for purification or further downstream workflows. In some embodiments, the lysis buffer 136 is added to the cells 132 in multiple passes, using either the entire volume of the lysis buffer 136, and/or portions thereof that are ultimately pooled together as the clarified lysate 154.

A reservoir 144 (FIGS. 1 and 4-7B) positioned on the first side 106 of the filter 104 provides sufficient volumetric capacity on the first side 106 of the filter 104 to contain the added lysis buffer 136, or at least portion thereof in an embodiment involving multiple lysis buffer addition steps. For example, the reservoir 144 may be sized to retain up to about 10-500 mL, or about 10, 20, 50, 75, 100, 250, 300, 350, 400, 450, or up to about 500 mL of fluid therein or any volume falling therebetween. In one embodiment, the reservoir 144 has a generally cylindrical body 146 with a conical portion 148 that tapers to direct fluid toward the filter 104. In one embodiment, the reservoir 144 and the filter 104 are arranged together within a unitary housing 150, which may be a user-replaceable lysis consumable 153 for an instrument 151, such as a manually-carryable bench top instrument, for performing the workflow 100. The instrument 151 may include any of a variety of ports 142 which can serve as intakes and/or outlets for fluids to and from the reservoir 144 and/or the filter 104. The ports 142 may also interface with an air supply 145 and/or a pressure sensor 147 (FIG. 7A and FIG. 7B) to monitor the workflow. Check valves 155 may be included to regulate fluid through the ports 142.

Figure 4:
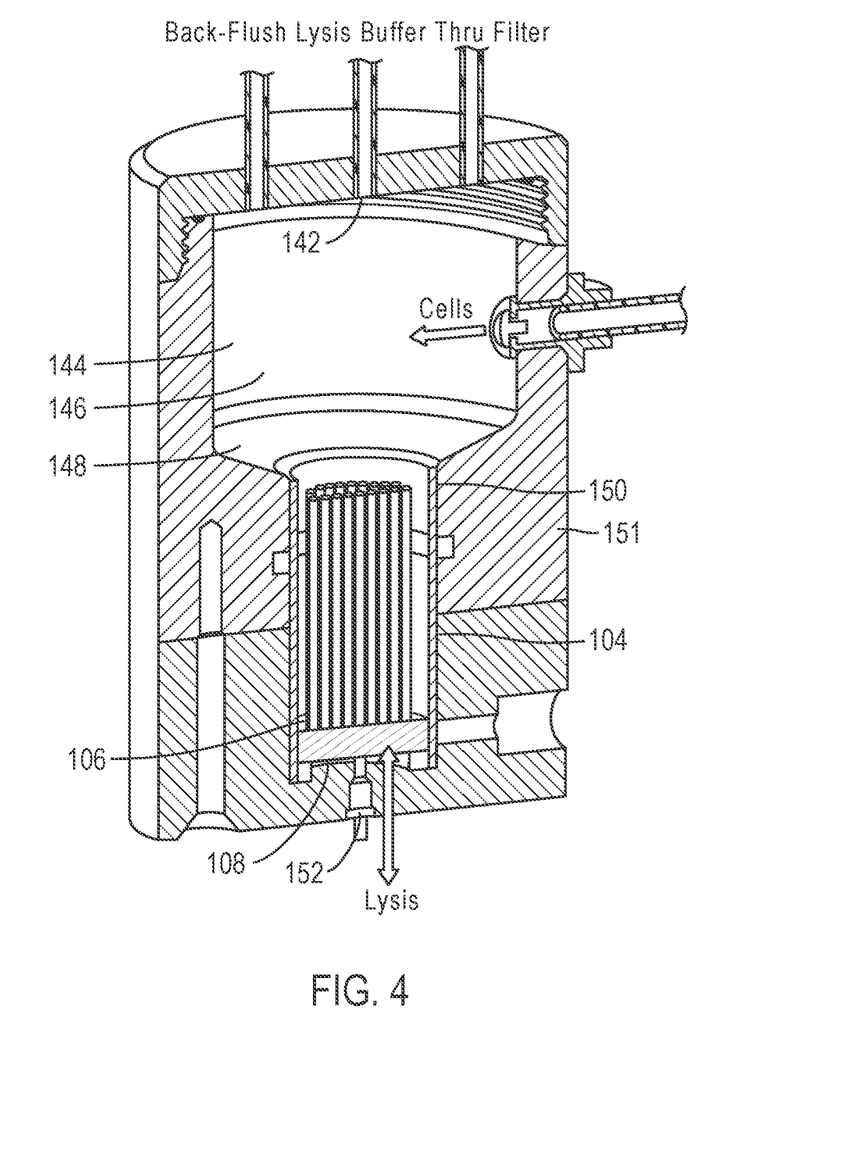
FIG. 4 depicts an embodiment of a reservoir-filter compatible with the workflows of FIG. 1 and FIG. 2.

Referring now to FIGS. 1 and 4-6, the lysis buffer 136 may be supplied from the holding chamber 140 to the reservoir 144 and the cells 132 on the first side 106 of the filter 104 using any of a variety of approaches. As shown in FIG. 4, in one case, the lysis buffer 136 is supplied to the reservoir 144 by "back-flushing" the lysis buffer 136 through the filter 104. The lysis buffer 136 is supplied from the holding chamber 140 by operating the reversible pump 112 in the second flow direction 116 to introduce the lysis buffer 136 through a port 152 that is in direct fluid communication with the second side 108 of the filter 104. The pump 112 drives the lysis buffer 136 into the lumens 130 of the hollow fibers 120 of the filter 104, and through the walls 128 thereof to reach the first side 106 of the filter 104 and the reservoir 144. Accordingly, the lysis buffer 136 passes through the filter 104 opposite the filtering direction through the filter 104 that was used to capture the cells 132. Back-flushing the lysis buffer 136 through the filter 104 in this manner simultaneously lyses the cells 132 and dislodges the cells 132 from the filter fibers 134 of the wall 128 of the filter 104 (FIG. 3A and FIG. 3B), thereby resuspending the cells 132 into the lysis buffer 136 for incubation in the reservoir 144 on the first side 106 of the filter 104. After incubation, the reversible pump 112 is operated in the first flow direction 114 to filter the lysate back through the filter 104 and out through the port 152, as earlier described, to obtain the clarified lysate 154 for purification or further downstream workflows. In one embodiment, the back-flushing procedure is repeated one or more additional times to improve yield.

Figure 5:
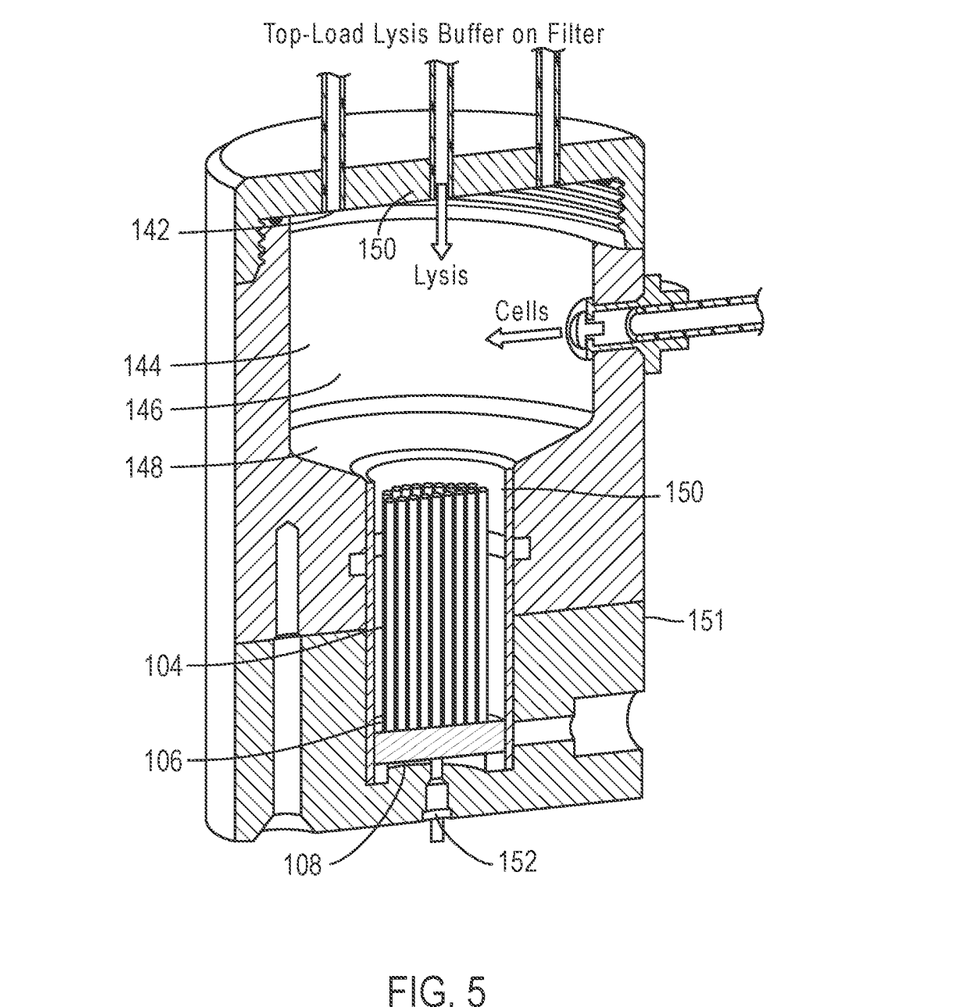
FIG. 5 depicts an alternate embodiment of a reservoir-filter compatible with the workflows of FIG. 1 and FIG. 2.

FIG. 5 depicts an alternate "top-loading" approach for supplying the lysis buffer 136 to the cells 132 on the filter 104. In this embodiment, the lysis buffer 136 is supplied directly to the first side 106 of the filter 104 from above, for example through a port 142 that is an intake 150 into the reservoir 144. The lysis buffer 136 may be supplied by operating the reversible pump 112 in the second flow direction 116 (FIG. 1). After incubation, the reversible pump 112 is operated in the first flow direction to drive and clarify the lysate through the filter 104 and out through the port 152 as earlier described. In this embodiment, the cells 132 are not resuspended and agitated in the lysis buffer 136 to the same degree as in the back-flushing embodiment (FIG. 4), so multiple passes of the lysis buffer 136 through the filter 104 may be necessary to achieve a suitable yield.

Figure 6:
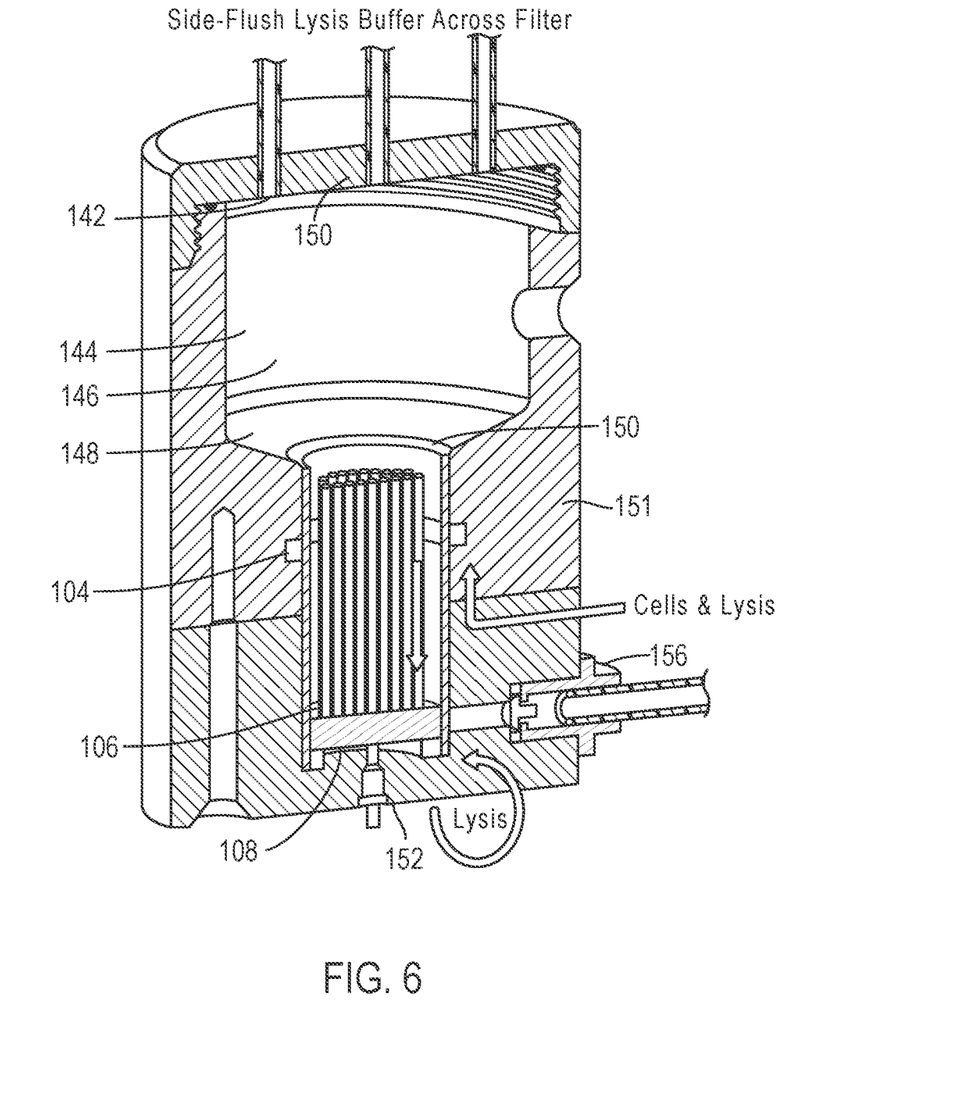
FIG. 6 depicts a further alternate embodiment of a reservoir-filter compatible with the workflows of FIG. 1 and FIG. 2.
Figure 7A:
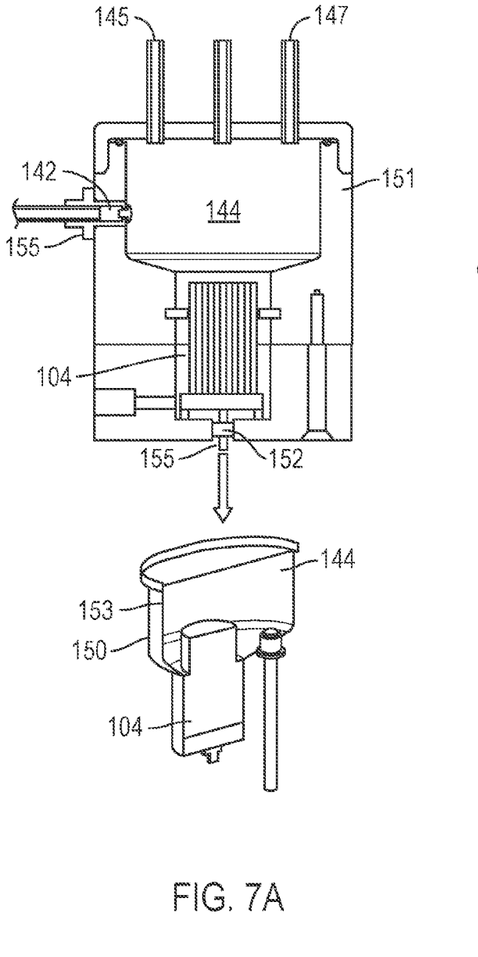
FIG. 7A and FIG. 7B depicts embodiments of portions of an instrument suitable for automatically performing the workflow of FIG. 2.
Figure 7B:
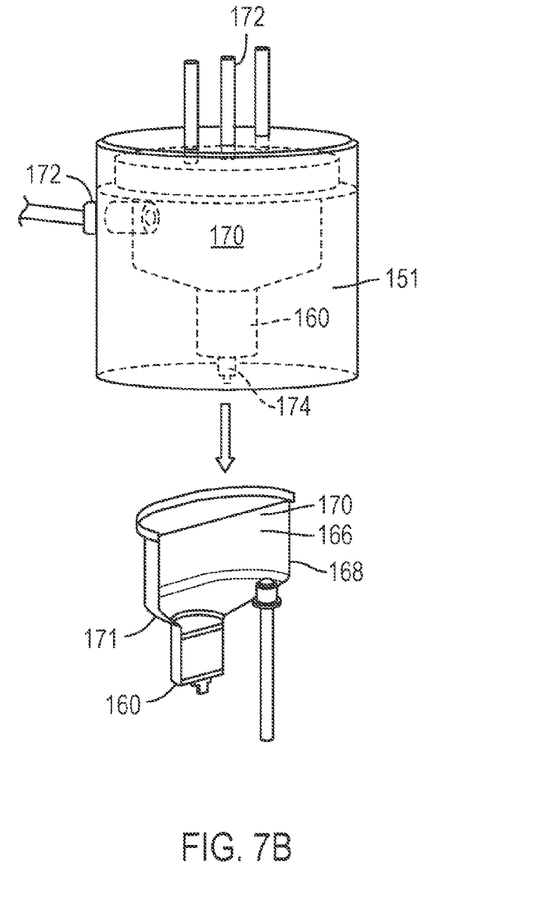

Further alternately, FIG. 6 depicts a "side-loading" approach for supplying the lysis buffer 136 to the cells 132 on the filter 104. In this embodiment, the lysis buffer 136 is supplied to the first side 106 of the filter 104, near the base of the filter 104 (e.g., near the end plug 122 in the embodiment of FIG. 3A and FIG. 3B). In the embodiment of FIG. 6, the lysis buffer 136 is added through an intake 156. Adding the lysis buffer 136 at this location generates a vortex effect within the filter 104 and increases agitation to dislodge the cells 132 from the wall 28 of the fibers 118 of the filter 104, without the need to back-flush fluid through the filter 104 from the second side 108 to the first side 106 thereof.

The workflow 100 may incorporate features of more than one of the lysis buffer 136 supply methods of FIGS. 4-6. For example, in one embodiment, the lysis step may begin with one or more back-flushing steps and incubation steps to simultaneously lyse and dislodge the cells 132 from the filter 104. Then, additional lysis buffer 136 (or, alternately, some or all of the lysate from the back-flushing step) may be added back through the reservoir 144 using the "top loading" methodology to rinse the filter 104 and avoid or minimize lysate loss from residual material left behind on the filter 104 after the back-flushing step(s).

Any acceptable lysis buffer known in the art may be used for the workflow 100 described herein. The selection of a suitable lysis buffer to properly lyse various types of cells is well within the skill level of the practitioner, and lysis buffers suitable for lysing bacterial cells, plant cells, fungal cells, yeast cell, animal cells, insect cells, dispersed cells and the like are known in the art. In one embodiment, the lysis buffer 136 is substantially free of proteases and contains at least one nuclease. The nuclease may be a DNase, or a combination of a DNase with an RNase, which can prevent problems with filter performance stemming from the release of double-stranded DNA (dsDNA) and the subsequent increase in cell lysate viscosity. Suitable enzymes include BENZONASE® (EMD), TURBEDNASE® (Life Technologies), and CYANASE® (RiboSolutions). One benefit of using CYANASE® is that the enzyme may be deactivated if desired upon completion of the lysis step. The lysis buffer 136 may further include any of a variety of additional additives and/or detergents as appropriate for the particular type of cell included in the cell suspension 102 and the target protein. In one embodiment, the lysis buffer includes pH 8.0 Tris buffer, NaCl, 3-[(3-cholamidopropyl)dimethylammonio]-1-propanesulfonate (CHAPS), β-D-thioglucopyranoside (OTGP), imidazole, and BENZONASE®.

Referring again to FIG. 1, the workflow 100 may optionally include one or more wash steps after the filtration of the cell suspension 102 through the filter 104 and before the addition of the lysis buffer 136. In this case, a suitable aqueous wash buffer 158 is passed through the filter 104 containing the capture cells 132 to remove protein or other components contaminating the captured cells 132. The wash buffer 158 may be supplied using any of the methodologies described above with respect to the lysis buffer 136. The wash buffer 158 may first be dispensed using the pump system 138 to the holding chamber 140, and then supplied to the filter 104 and reservoir 144 by the pump 112 in the second flow direction 116. The wash buffer 158 may rinse the cells 132 using the "back-flushing," "top-loading," and/ or "side-loading" methodologies, or combinations thereof.

Figure 2:
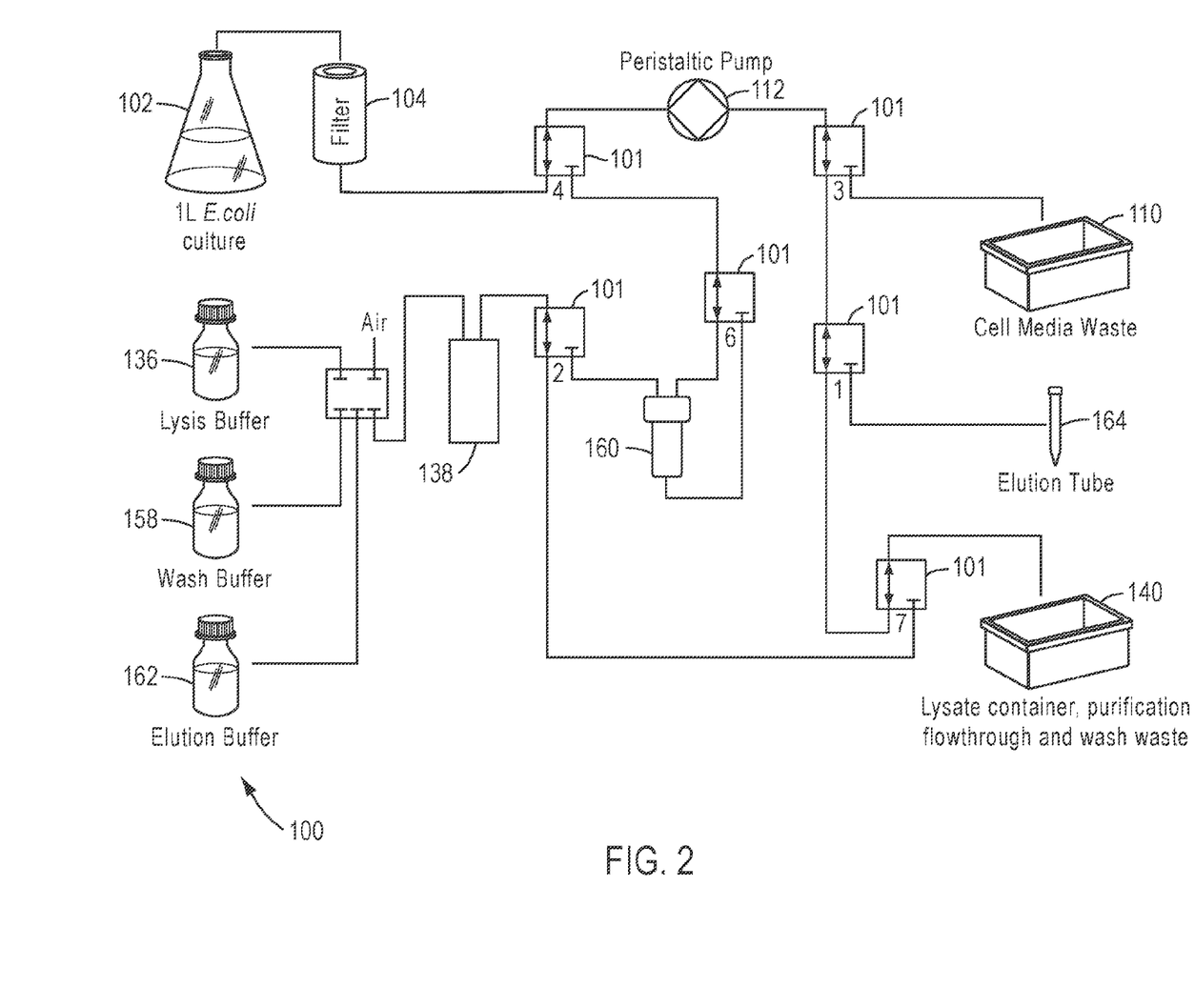
FIG. 2 schematically depicts one embodiment of a cell lysis and protein purification workflow.

Referring now to FIG. 2, which depicts an embodiment of the disclosed workflow generally designated 100', the workflow 100' may further include purifying a protein or other target material from the clarified lysate 154. The protein may be purified using any method known in the art, such as chromatography through the use of a purification column 160, including but not limited to affinity chromatography, gel filtration chromatography, and ion exchange chromatography, or a combination thereof. In one embodiment, the protein is purified using affinity chromatography methodology, where the purification column 160 is loaded with a charged resin, such as MC20 POROS® (Applied Biosystems, LLC) resin activated with nickel sulfate.

To purify the protein product from the clarified lysate 154, the reversible pump 112 and/or the pump system 138 can be activated to direct the clarified lysate 154 from the filter 104 and to load the clarified lysate 154 onto the purification column 160. The target protein product is retained on the column 160, while the remainder of the lysate fluid passes through the column 160. The clarified lysate 154 may be cycled through the purification column 160 multiple times to improve the yield. Once purification is complete, the remaining liquid may be pumped to the waste receptacle 110 and discarded. Wash buffer 158 may optionally be cycled through the purification column 160 one or more times. The target protein may then be eluted from the purification column 160 with an elution buffer 162 of any suitable type known in the art, which in one embodiment may include pH 8.0 Tris buffer, NaCl, and imidazole. In one embodiment, the target protein is eluted in about 5 mL of elution buffer, or less. The protein-containing eluent may then be directed via the reversible pump 112 and/or pump system 138, and/or manually, for collection in an elution tube 164 for further downstream workflows.

Referring again to FIG. 7A and FIG. 7B, an automated embodiment incorporating the workflow 100' may be contained with a single instrument 151, which in one case may be a manually-carryable bench top instrument. The purification column 160 may be included in a user-replaceable purification consumable 166 for insertion into the instrument 151. In one embodiment, the purification consumable 166 has a housing 168 that includes the purification column 160 and a reservoir 170 to receive and retain a volume of clarified lysate 154 or other fluid to loaded to or otherwise passed through the column 160. The reservoir 170 may be generally cylindrical in shape, and include a tapered conical portion 171 to facilitate liquid flow from the reservoir 170 into the purification column 160. The portion of the instrument 151 which receives the purification consumable 166 may include features similar to those described above with respect to the portion of the instrument 151 that receives the lysis consumable 153. For example, this portion of the instrument 151 may include any of a variety of ports 172 to serve as intakes for fluids to enter the reservoir 170 or to interface with an air supply and/or a pressure sensor to control and monitor the workflow 100'. An outlet 174 is positioned to facilitate flow of liquids out of the column 160.

In some embodiments, any of the individual steps of the workflows 100, 100' described above may be performed manually by a user or users who may monitor the progression and/or the completion thereof. Optionally, in some embodiments any one or more of the individual steps of the workflows 100, 100' may be automated and may operate independently of any user monitoring or input, aside from, in one case, stocking the liquid components 102, 136, 158, 162. In one embodiment of an automated workflow 100, 100', the process may be controlled by a touch screen computer running LABVIEW® (National Instruments corporation) software, or other suitable software capable of directing and controlling the various steps of the workflow 100, 100'.

In one embodiment of an automated workflow 100, 100' the workflow is performed substantially entirely within the instrument 151, for example a manually-carryable bench top instrument that is configured to receive the lysis consumable 153 and/or the purification consumable 166. In some embodiments, the sources of the various fluids and buffers 102, 136, 158, 162, and/or various collection vessels such as the holding chamber 140, elution tube 164, and/or a container for the clarified lysate 154, may be positioned external to the instrument 151 but fluidly connected thereto through suitable ports and valve systems. The instrument 151 may be operatively connected to a controller loaded with software for automating the workflow 100, 100' and a user interface to provide control and monitoring capabilities over the progress and specific functional parameters of the workflow 100, 100'.

In one embodiment of an automated workflow, the entire lysis process, including filtration of up to at least 1 liter of the cell suspension 102, any optional wash steps using the wash buffer 158, all steps related to loading the lysis buffer 136 into the reservoir 144 for incubation and/or resuspension of captured cells 132 and lysing the cells 132, and collection of the clarified lysate 154 are completed in 2 hours or less. In one embodiment, all steps involved in collecting a purified target protein from the clarified lysate 154, including purification of the target protein through the purification column 160, with all wash and elution steps, are completed in about 2 hours or less. Accordingly, in one embodiment, filtration, lysis, clarification, and purification of a target protein from up to at least 1 liter of cell suspension 102 may be completed in a single automated process in about 4 hours or less. The workflow 100, 100' is scalable to accommodate filtration and/or purification requirements for volumes of cell suspension 102 greater than 1 liter by increasing the size and/or number of the various system components.

The embodiments of this invention shown in the drawings and described above are exemplary of numerous embodiments that may be made within the scope of the appended claims. It is contemplated that numerous other configurations of the disclosure may be created taking advantage of the disclosed approach. In short, it is the applicants' intention that the scope of the patent issuing herefrom will be limited only by the scope of the appended claims.

What is claimed is:

1. A cell lysis workflow comprising the steps of:
   a) passing a cell suspension through a filter in a first flow direction from a first side of the filter toward a second side thereof, wherein the filter captures a plurality of cells on the first side;
   b) passing a lysis solution through the filter in a second flow direction opposite the first direction, thereby dislodging the plurality of cells captured on the filter and resuspending the plurality of cells in the lysis solution on the first side of the filter, wherein the lysis solution lyses the plurality of cells to produce a cellular lysate;
   c) passing the cellular lysate through the filter in the first flow direction; and
   d) obtaining a clarified lysate.

2. The cell lysis workflow of claim 1, wherein steps a) through c) are carried out automatically.

3. The cell lysis workflow of claim 2, wherein the process further comprises isolating a protein from the cellular lysate.

4. The cell lysis workflow of claim 1, further comprising, between steps a) and b), passing a wash solution through the filter in the first flow direction.

5. The cell lysis workflow of claim 1, further comprising, between steps b) and c), incubating the cellular lysate for a predetermined period of time.

6. The cell lysis workflow of claim 1, further comprising isolating or purifying a protein from the cellular lysate.

7. The cell lysis workflow of claim 6, wherein the protein is isolated by column chromatography selected from the group consisting of affinity chromatography, gel filtration chromatography, and ion exchange chromatography, or a combination thereof.

8. The cell lysis workflow of claim 1, wherein the filter is a hollow fiber filter.

9. The cell lysis workflow of claim 1, further comprising providing a reversible pump, wherein the reversible pump is operable to selectively cause fluid to pass through the filter in the first flow direction or the second flow direction.

10. The cell lysis workflow of claim 9, wherein the reversible pump is a peristaltic pump.

11. The cell lysis workflow of claim 1, further comprising providing a reservoir on the first side of the filter, wherein the reservoir receives the cellular lysate during step b).

12. The cell lysis workflow of claim 1, wherein the cell suspension comprises eukaryotic cells selected from the group consisting of rodent, primate, and human cells.

13. The cell lysis workflow of claim 1, wherein the cell suspension comprises prokaryotic cells.

14. The cell lysis workflow of claim 1, wherein the lysis solution contains at least one lysis agent and a DNase.

* * * * *